United States Patent
Ward et al.

(10) Patent No.: US 8,064,610 B2
(45) Date of Patent: Nov. 22, 2011

(54) AMBIENT NOISE CANCELING PHYSIOLOGICAL ACOUSTIC MONITORING SYSTEM AND METHOD

(75) Inventors: Russell C. Ward, Sun Prairie, WI (US); Parry W. Heide, Madison, WI (US); Bruce E. Dammann, Middleton, WI (US)

(73) Assignee: The General Electric Company, Schenectady, NY (US)

( * ) Notice: Subject to any disclaimer, the term of this patent is extended or adjusted under 35 U.S.C. 154(b) by 1888 days.

(21) Appl. No.: 11/169,480

(22) Filed: Jun. 29, 2005

(65) Prior Publication Data

US 2007/0003072 A1 Jan. 4, 2007

(51) Int. Cl.
*A61B 7/04* (2006.01)
*H03G 3/20* (2006.01)
(52) U.S. Cl. ............ 381/67; 381/57; 381/71.3; 600/586
(58) Field of Classification Search .................... 381/67, 381/57, 61, 71.1, 71.3, 71.7; 600/528, 586
See application file for complete search history.

(56) References Cited

U.S. PATENT DOCUMENTS

| | | | | |
|---|---|---|---|---|
| 5,309,922 A * | 5/1994 | Schechter et al. | ............ | 600/534 |
| 5,427,102 A * | 6/1995 | Shimode et al. | .............. | 600/410 |
| 5,492,129 A * | 2/1996 | Greenberger | ................. | 600/528 |
| 6,132,381 A * | 10/2000 | Forbes et al. | ................. | 600/483 |
| 6,179,792 B1 * | 1/2001 | Krause | ............... | 601/2 |
| 6,408,978 B1 * | 6/2002 | Premus | ......................... | 181/120 |
| 6,478,744 B2 * | 11/2002 | Mohler | ......................... | 600/485 |
| 6,897,781 B2 * | 5/2005 | Cooper et al. | .............. | 340/573.1 |
| 7,031,857 B2 * | 4/2006 | Tarassenko et al. | ............ | 702/67 |
| 7,520,861 B2 * | 4/2009 | Murphy | ........................ | 600/529 |
| 2004/0037429 A1 * | 2/2004 | Candioty | .......................... | 381/67 |
| 2006/0198533 A1 * | 9/2006 | Wang et al. | ........................ | 381/67 |

* cited by examiner

*Primary Examiner* — Xu Mei
(74) *Attorney, Agent, or Firm* — Andrus, Sceales, Starke & Sawall, LLP

(57) ABSTRACT

The present invention is an ambient noise canceling physiological acoustic monitoring system and method. The system and method utilizes a plurality of microphones to collect input data including ambient noise signals, bed frame noise signals and patient respiratory and cardiac data signals. The system and method cancels the ambient noise and bed frame noise signals, and calculates a filtered audio output signal with an algorithm that utilizes ECG rhythm patterns and impedance pneumography. The set of input data and the filtered audio output signal are then displayed in real time.

18 Claims, 3 Drawing Sheets

AMBIENT NOISE CANCELING PHYSIOLOGICAL ACOUSTIC MONITORING SYSTEM AND METHOD

FIELD OF THE INVENTION

The present invention relates to patient monitoring. More particularly, the invention relates to the field of noise cancellation and display in patient monitoring systems.

BACKGROUND OF THE INVENTION

The ability of clinicians to use conventional stethoscopes to hear and assess patient heart and breath sounds is significantly diminished or simply impossible in high ambient noise environments like aircraft or ambulance transport applications. The combination of ambient decibel level along with audio and vibration frequencies mean that clinicians cannot use this fundamental method to assess the patient's condition. This invention is intended to overcome both ambient noise and vibration frequencies to enable clinicians to assess heart and breath sounds adequately in such noisy environments.

SUMMARY OF THE INVENTION

The present invention is an ambient noise canceling physiological acoustic monitoring system and method. The system and method utilizes a plurality of microphones to collect input data including ambient noise signals, bed frame noise signals and patient respiratory and cardiac data signals. The system and method cancels the ambient noise and bed frame noise signals, and calculates a filtered audio output signal with an algorithm that utilizes ECG rhythm patterns and impedance pneumography. The set of input data and the filtered audio output signal are then displayed in real time.

In one aspect of the present invention, a method of canceling noise with a physiological acoustic monitor comprises collecting a set of input data from a set of input microphones, canceling a frame noise signal and an ambient noise signal from the set of input data, calculating a filtered audio output signal and displaying the audio output signal and the set of input data in real time on a display. The set of input data further includes a patient data signal, wherein the patient data signal includes a bilateral lung signal and a cardiac signal. The method further comprises amplifying the filtered audio output signal and the set of input data and routing the filtered audio output signal and the set of input data to the display, wherein the calculating step further comprises collecting an ECG signal and an impedance pneumography signal to distinguish an onset and an offset and synchronizing the onset and offset. The set of input microphones include a patient microphone, a frame microphone, and an ambient microphone, and further comprises stopping the real time display such that the filtered audio output signal may be viewed in a defined timeframe, storing the filtered audio output signal in a storage device, printing the filtered audio output signal, replaying the filtered audio output on the display and matching the audio output signal against a set of known sound templates.

In another aspect of the present invention, a physiological acoustic monitoring system for canceling noise comprises a set of input microphones configured to collect a set of input data, a processor configured to receive the set of input data, wherein the processor cancels a frame noise signal and an ambient noise signal from the set of input data and further wherein the processor calculates a filtered audio output signal, and a display configured to receive the filtered audio output signal and the set of input data, further configured to display the filtered audio output signal and the set of input data in real time. The set of input data includes a patient data signal and further wherein the patient data signal includes a bilateral lung signal and a cardiac signal. The processor is further configured to amplify the filtered audio output signal, route the filtered audio output signal and the set of input data to the display, collect an ECG signal and an impedance pneumography signal to distinguish an onset and an offset, and synchronizing the onset and the offset. The set of input microphones includes a patient microphone, a frame microphone, and an ambient microphone.

The display is further configured to stop the real time display of the filtered audio output signal such that the filtered audio output signal may be viewed in a defined timeframe. The system further comprises a storage device configured for storing the filtered audio output signal and a printer configured to print the filtered audio output signal, wherein the display is further configured to replay the filtered audio output and wherein the display is further configured to match the filtered audio output signal against a set of known sound templates.

In yet another aspect of the present invention, a method of physiological acoustic monitor noise cancellation comprises collecting a set of input data from a set of input microphones, canceling a frame noise signal and an ambient noise signal from the set of input data, collecting an ECG signal and an impedance pneumography signal to distinguish an onset and an offset, synchronizing the onset and the offset, thus calculating a filtered audio output signal, amplifying the filtered audio output signal and the set of input data, routing the filtered audio output signal and the set of input data to the display, and displaying the filtered audio output signal and the set of input data in real time on the display.

DETAILED DESCRIPTION OF THE PRESENT INVENTION

Figure 1:
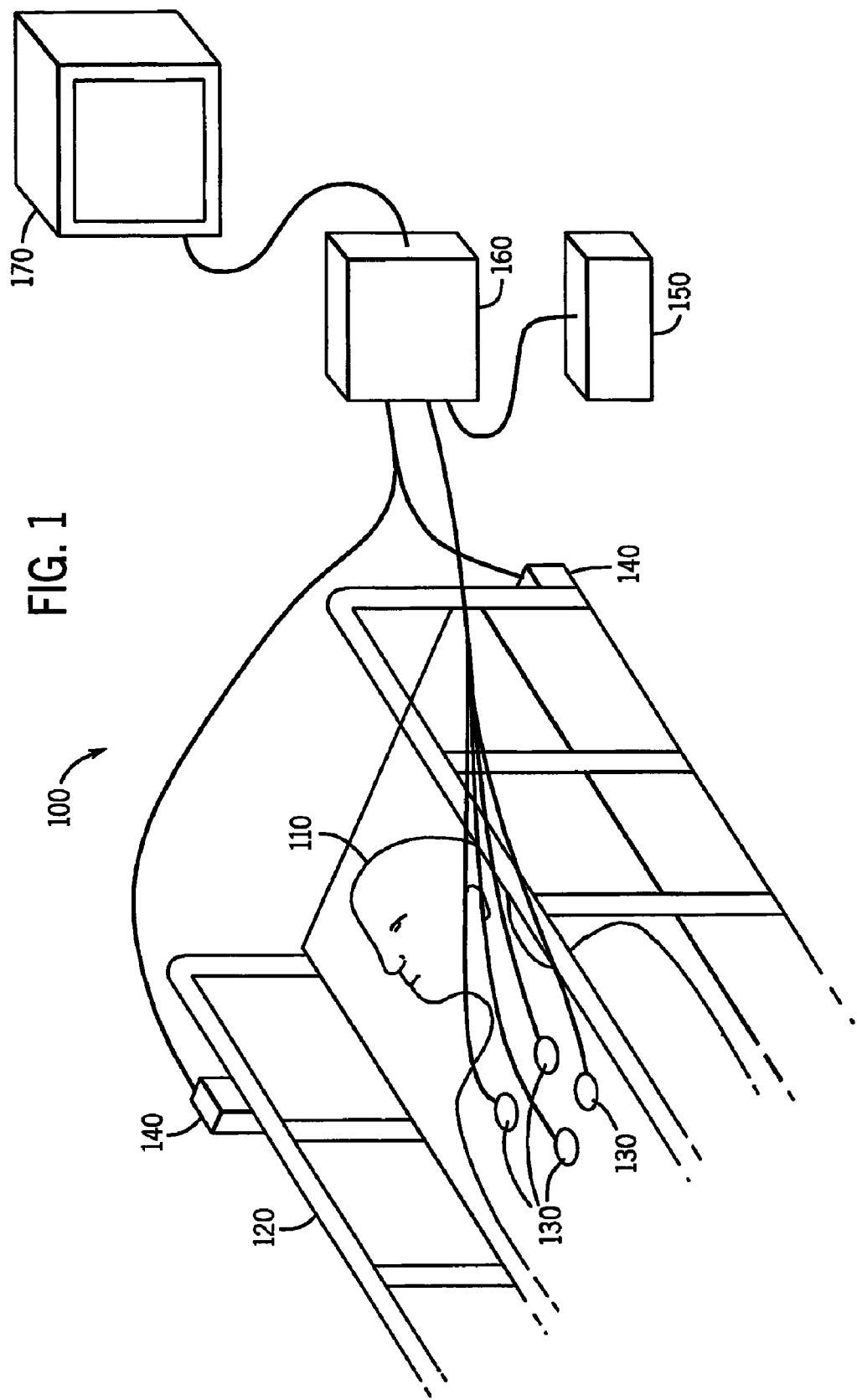
FIG. 1 is a graphical representation of a system according to an embodiment of the present invention.

The system and method of the present invention is an ambient noise canceling physiological acoustic monitor that uses a series of microphones to monitor multiple channels of real time sound frequencies from a patient (heart and breath sounds). The patient audio input channel also has provisions for the positioning of two bilateral microphones that listen to each lung independently. The ambient environment is also monitored (immediately adjacent to the patient microphone), as well as the audible vibration frequencies from the patient bed/stretcher that are transferred from surrounding structures that are generated by engines, transmissions, generators and other noise sources in the environment. This acquired patient noise data is then processed using noise cancellation technology to filter noise from an ambient noise microphone that is positioned close to, but insulated from, direct contact with the patient, a vibration frequency microphone attached to the stretcher or bed frame on which the patient is positioned and an algorithm that utilizes ECG rhythm patterns and impedance pneumography to reference (synchronize) onset and offset cardiac and lung electrical signals as landmarks for the recognition of commencement and cessation of the respective cardiac and lung sounds. These physiological signals are derived either from an integrated or standalone electrocardiograph fitted with the impedance pneumography parameters.

The resulting audio data could be represented and displayed in a number of ways. Preferably, following the application of noise cancellation and signal recognition filters, the resulting representations for cardiac and breath sounds are amplified and routed to an audio channel output where the clinician controls the volume and listens to the sounds with headphones. All four processed noise frequencies (cardiac, lung, ambient and vibration) are then displayed real time on a graphical display to provide a visual representation of these physiological sounds and to reinforce the audio output. These can be displayed as a cascading trace on a physiological monitor display, which can then be stopped for review, recorded to printer, trended to memory and replayed through the audio channel for further consultations. The resulting respiratory signals can also be matched against known respiratory sound templates to diagnose pulmonary conditions such as asthma (wheezing) or bronchial tones from which user alerts can be triggered from within the device this acoustic monitoring parameter is incorporated.

The system and method of ambient noise canceling physiological acoustic monitoring of the present invention can be implemented as a stand-alone device or as a module that is integrated into a configured or modular multi-parameter physiological monitor or in a ventilation system used to ventilate patients with respiratory compromise. These devices may all be standalone devices or incorporated into a local area network. The microphones used for patient monitoring are preferably integrated into a reusable pad assembly that can be placed under the patient's thorax or on the patient's chest and secured with a single use adhesive tape. An alternative disposable pad microphone pad assembly can also be used.

FIG. 1 is a graphical representation of an embodiment of the present invention. In FIG. 1, the monitoring system 100 is used to monitor a patient 110. At least one patient microphone 130 is configured to receive cardiac and respiratory signals from the patient 110 and send those signals to the processor 160. Likewise, a bed frame microphone 140 is configured to receive a noise signal from the bed frame and send it to the processor 160. The bed frame microphone 140 may be attached to any part of the bed frame 120. However, the bed frame microphone 140 is better suited to be attached to the bed frame 120 where the bed frame 120 is unlikely to be used as a handle or a portion that receives a lot of contact with a physician or emergency medical transporter.

Still referring to FIG. 1, an ambient microphone 150 is configured to receive ambient noise signals and to further transmit the ambient noise signals to the processor 160. The processor 160 processes the signals from the patient microphone 130, the bed frame microphone 140, and the ambient microphone 150, and sends the resulting audio output signal to the monitor 170. The monitor 170 provides a graphical representation of the output noise signal, so that a physician or other medical personnel can visually read the audio output signal without actually hearing the audio output signal. It should be noted that the bed frame 120 may also include any frame structure of either a hospital bed or gurney or stretcher, as is commonly used in a hospital or medical transportation vehicle. Furthermore, the patient microphone 130, the bed frame microphone 140 and the ambient microphone 150 are preferably configured as depicted in FIG. 1. However, these microphones 130, 140, 150 may be configured in further embodiments to conform with the particular monitoring system 100, i.e., the bed frame microphone 140 may be attached to a portion of the bed frame 120 under the patient, or the ambient microphone 150 can be coupled to the gurney or stretcher in order to keep the ambient microphone 150 out of high traffic areas. Likewise, the processor 160 can be attached to the gurney or bed, or to the display 170, or be incorporated as a standalone device.

Figure 2:
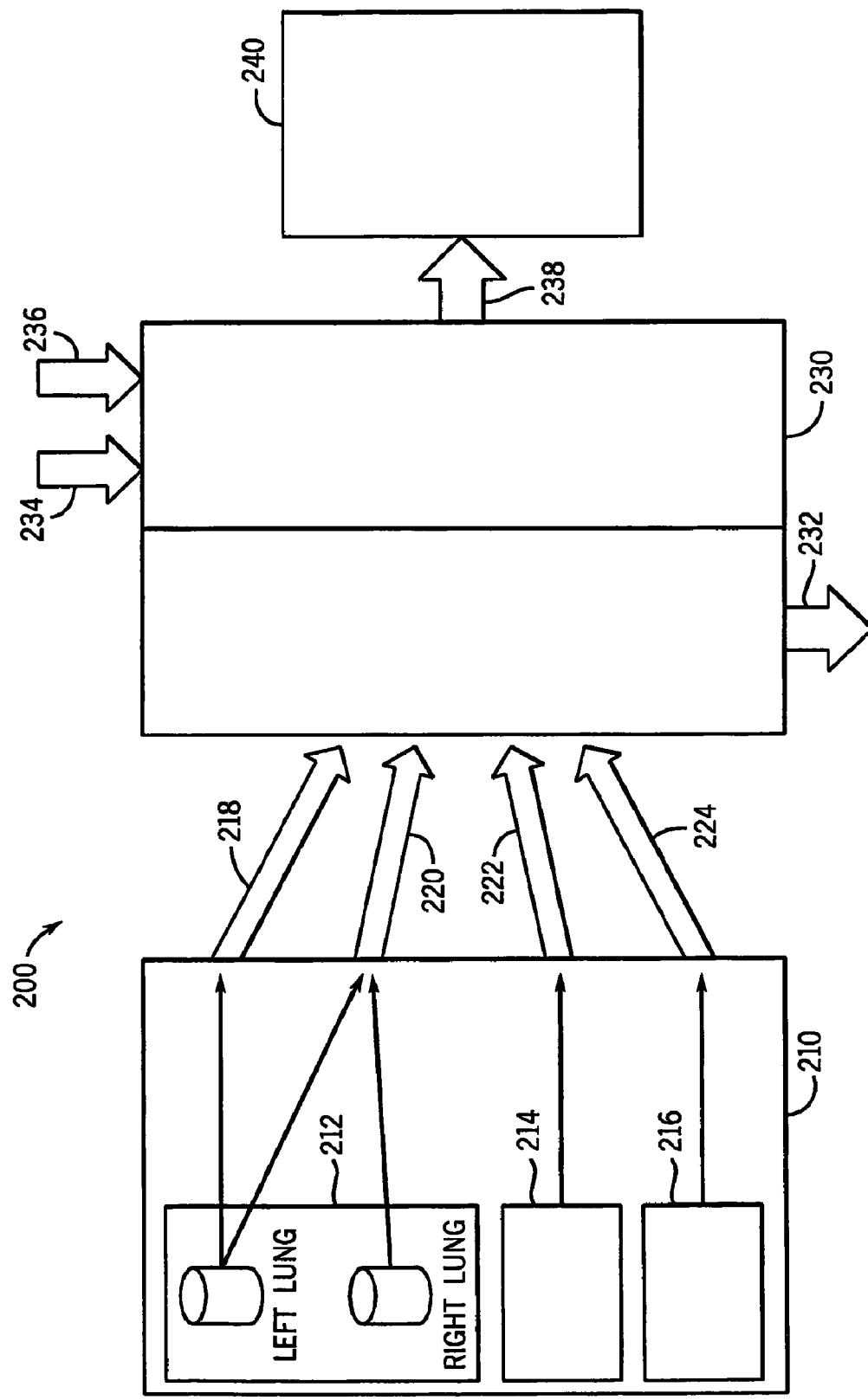
FIG. 2 is a block diagram of a system according to an embodiment of the present invention.

FIG. 2 depicts a block diagram of the monitoring system 200 of the present invention. Here, the input microphones 210 include the patient microphone 212, the bed frame microphone 214 and the ambient microphone 216. The patient microphone 212 outputs to the processor 230 both a cardiac signal 218 and a lung data signal 220. The bed frame microphone 214 outputs a bed frame noise signal 222, and the ambient microphone 216 outputs an ambient noise signal 224. The processor 230 receives these signals 218, 220, 222, 224 and the processor 230 utilizes noise cancellation technology to filter the ambient noise and the bed frame noise. The canceled noise signals 232 are removed from the input signals 218, 220, 222, 224. An ECG input 234 and an impedance pneumography input 236 are inputted into the processor 230, and are utilized in an algorithm with the noise canceled input signals 218, 220, 222, 224 to produce a filtered audio output 238. The filtered audio output 238 is then inputted into the display 240, so that a visual representation of the filtered audio output 238 can be monitored by a physician or medical caregiver.

Figure 3:
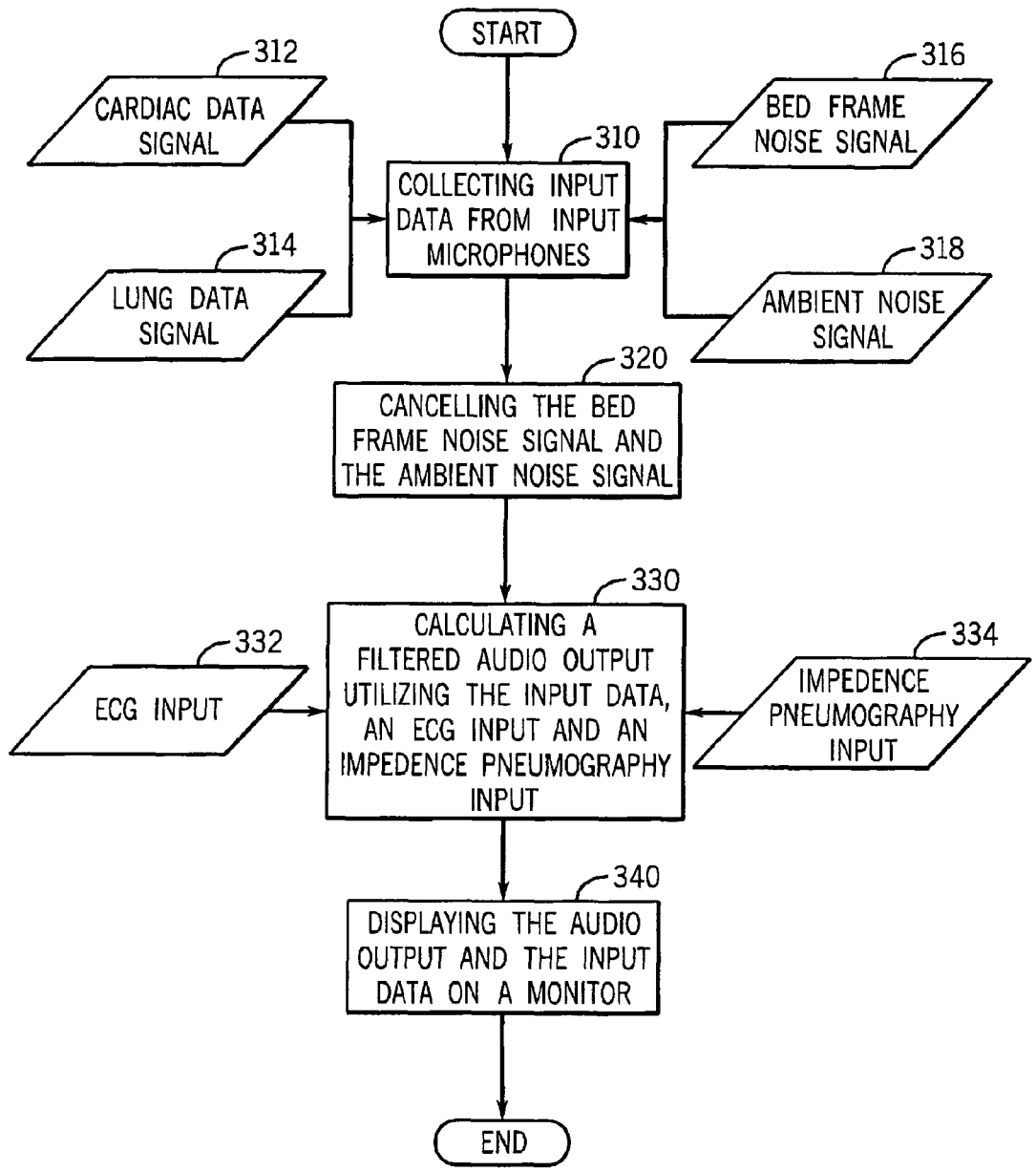
FIG. 3 is a flow chart of a method according to an embodiment of the present invention.

The method of the present invention is depicted in FIG. 3. In step 310, inputs are collected from input microphones. The inputs collected in step 310 include cardiac data signal 312, the lung data signal 314, the bed frame noise signal 316 and the ambient noise signal 318. In step 320 the bed frame noise signal and the ambient noise signal are canceled in the processor. In step 330 a filtered audio output is calculated utilizing the input data, as well as an ECG input 332 and an impedance pneumography input 334. Lastly, in step 340 the audio output and the input data are displayed on a monitor.

Unlike prior art models the acoustic parameter of the present invention allows the electronic monitoring of a task that has been traditionally performed manually. Therefore, the data can be managed, recorded, displayed, saved and used for other calculations. By design, the acoustic monitoring parameter of the present invention can therefore be used in situations where there are levels of high ambient noise. Currently, there are no other acoustic listening devices that will allow clinicians to successfully hear heart and lung sounds of patients traveling in aircraft or ambulances in a visual format. Furthermore, the system and method of the present invention also allows the electronic recording of sound wave patterns in a visual format that can be displayed and observed on a physiological monitor. Further, these sound representations can be stored as trends and later reviewed and "played back" for clinical diagnostic and teaching purposes by other clinicians.

The system and method of the present invention uses dual channels for noise ambient noise collection: one for ambient and one for vibration frequency passed via the stretcher/bed, and bilateral lung microphones to facilitate differentiation of air entry in each lunch and dual channel (stereo) recording of cardiac sounds simultaneously. The cascading visual display of the filtered, ECG and impedance pneumography synchronized sound waveforms on a single monitor display the ability to trend continuous cardiac and lung sounds for visualization and playback to aid diagnosis and training and the use of monitored audible sound to trigger advisory messages to clinicians of lung and cardiac condition changes and suctioning needs as a part of a decision support tool are clear advantages of the system and method of the present invention.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of canceling noise with a physiological acoustic monitor, the method comprising:
   collecting a set of input data from a set of input microphones;
   canceling a bed frame noise signal and an ambient noise signal from the set of input data;
   calculating a filtered audio output signal;
   collecting an ECG signal and an impedance pneumography signal to distinguish an onset and an offset;
   synchronizing the onset and the offset; and
   displaying the filtered audio output signal and the set of input data in real time on a display.

2. The method as claimed in claim 1, wherein the set of input data includes a patient data signal, further wherein the patient data signal includes:
   a bilateral lung signal; and
   a cardiac signal.

3. The method as claimed in claim 1, further comprising:
   amplifying the filtered audio output signal and the set of input data; and
   routing the filtered audio output signal and the set of input data to the display.

4. The method as claimed in claim 1, wherein the set of input microphones include:
   a patient microphone;
   a bed frame microphone; and
   an ambient microphone.

5. The method as claimed in claim 1, further comprising stopping the real time display to display a defined timeframe of the filtered audio output signal.

6. The method as claimed in claim 1, further comprising storing the filtered audio output signal in a storage device.

7. The method as claimed in claim 1, further comprising printing the filtered audio output signal.

8. The method as claimed in claim 1, further comprising replaying the filtered audio output on the display.

9. The method as claimed in claim 1, further comprising matching the filtered audio output signal against a set of known sound templates.

10. A physiological acoustic monitoring system for canceling noise, the system comprising:
    a set of input microphones configured to collect a set of input data;
    a processor configured to receive the set of input data, wherein the processor cancels a bed frame noise signal and an ambient noise signal from the set of input data and the processor calculates a filtered audio output signal, further wherein the processor is configured to amplify the filtered audio output signal, route the filtered audio output signal and the set of input data to the display, collect an ECG signal and an impedance pneumography signal to distinguish an onset and an offset, and synchronize the onset and the offset; and
    a display configured to receive the filtered audio output signal and the set of input data, and further configured to display the filtered audio output signal and the set of input data in real time.

11. The system as claimed in claim 10, wherein the set of input data includes a patient data signal, further wherein the patient data signal includes:
    a bilateral lung signal; and
    a cardiac signal.

12. The system as claimed in claim 10, wherein the set of input microphones includes:
    a patient microphone;
    a bed frame microphone; and
    an ambient microphone.

13. The system as claimed in claim 10, wherein the display is further configured to stop the real time display to display a defined timeframe of the filtered audio output signal.

14. The system as claimed in claim 10, further comprising a storage device configured for storing the filtered audio output signal.

15. The system as claimed in claim 10, wherein the set of input microphones comprises:
    a patient microphone configured to collect a patient data signal;
    a bed frame microphone configured to collect the bed frame noise signal; and
    an ambient microphone configured to collect the ambient noise signal;
    wherein the processor removes the bed frame noise signal and the ambient noise signal from the patient data signal to calculate the filtered audio output signal.

16. The system as claimed in claim 15, wherein the patient microphone is configured for attachment to a patient, the bed frame microphone is configured for attachment to a patient bed frame, and the ambient microphone is insulated from the patient.

17. The system as claimed in claim 16, wherein the processor uses noise cancellation to remove the bed frame noise signal and the ambient noise signal from the patient data signal.

18. A method of physiological acoustic monitor noise cancellation, the method comprising:
    collecting a set of input data from a set of input microphones;
    canceling a bed frame noise signal and an ambient noise signal from the set of input data;
    collecting an ECG signal and an impedance pneumography signal to distinguish an onset and an offset;
    synchronizing the onset and the offset, thus calculating a filtered audio output signal;
    amplifying the filtered audio output signal and the set of input data;
    routing the filtered audio output signal and the set of input data to the display; and
    displaying the filtered audio output signal and the set of input data in real time on the display.

* * * * *